US012636327B2

(12) United States Patent
Brandsborg et al.

(10) Patent No.: US 12,636,327 B2
(45) Date of Patent: May 26, 2026

(54) **PROBIOTIC COMPOSITION FOR TREATMENT OF ORAL *CANDIDA* INFECTIONS**

(71) Applicant: ADM Denmark A/S, Hundested (DK)

(72) Inventors: Erik Brandsborg, Holbæk (DK); Lasse Sommer Mikkelsen, Frederiksværk (DK)

(73) Assignee: ADM Denmark A/S, Hundested (DK)

( * ) Notice: Subject to any disclaimer, the term of this patent is extended or adjusted under 35 U.S.C. 154(b) by 454 days.

(21) Appl. No.: 18/001,243

(22) PCT Filed: Jun. 10, 2021

(86) PCT No.: PCT/EP2021/065710
§ 371 (c)(1),
(2) Date: Dec. 8, 2022

(87) PCT Pub. No.: WO2021/250208
PCT Pub. Date: Dec. 16, 2021

(65) Prior Publication Data
US 2023/0302066 A1 Sep. 28, 2023

(30) Foreign Application Priority Data
Jun. 11, 2020 (EP) .................................... 20179563

(51) Int. Cl.
| | |
|---|---|
| *A61K 35/747* | (2015.01) |
| *A61P 31/10* | (2006.01) |
| *C12N 1/205* | (2026.01) |
| *C12R 1/225* | (2006.01) |

(52) U.S. Cl.
CPC ............ *A61K 35/747* (2013.01); *A61P 31/10* (2018.01); *C12N 1/205* (2021.05); *C12R 2001/225* (2021.05)

(58) Field of Classification Search
CPC ....... A61K 35/747; A61P 31/10; C12N 1/205; C12R 2001/225
See application file for complete search history.

(56) References Cited

FOREIGN PATENT DOCUMENTS

WO WO 2017/001440 A1 1/2017

OTHER PUBLICATIONS

International Search Report mailed Sep. 9, 2014 in International Application No. PCT/EP2021/065710.
Martinez et al., "Improved treatment of vulvovaginal candidiasis with fluconazole plus probiotic *Lactobacillus rhamnosus* GR-1 and *Lactobacillus reuteri* RC-14", Letters in Applied Microbiology, 2009, vol. 48, pp. 269-274.
Jørgensen et al., "*Lactobacillus rhamnosus* strains of oral and vaginal origin show strong antifungal activity in vitro", Journal of Oral Microbiology, 2020, vol. 12, 1832832, in 9 pages.
Zangl et al., "The role of *Lactobacillus* species in the control of Candida via biotrophic interactions", Microbial Cell, Jan. 2020, vol. 7, No. 1, pp. 1-14.

*Primary Examiner* — Louise W Humphrey
*Assistant Examiner* — Rachel Emily Martin
(74) *Attorney, Agent, or Firm* — Knobbe Martens Olson & Bear LLP

(57) ABSTRACT
The present invention relates to a *Lactobacillus rhamnosus* strain. In particular, the present invention relates to a composition comprising a *Lactobacillus rhamnosus* optionally in combination with a further lactobacilli and the use of the same in the treatment, prevention or alleviation of candidiasis.

16 Claims, 7 Drawing Sheets

PROBIOTIC COMPOSITION FOR TREATMENT OF ORAL *CANDIDA* INFECTIONS

CROSS REFERENCE TO RELATED APPLICATIONS

This application is a U.S. National Phase Application of PCT International Application Number PCT/EP2021/065710, filed on Jun. 10, 2021, designating the United States of America and published in the English language, which is an International Application of and claims the benefit of priority to European Patent Application No. 20179563.0, filed on Jun. 11, 2020. The disclosures of the above-referenced applications are hereby expressly incorporated by reference in their entireties.

FIELD OF THE INVENTION

The present invention relates to a *Lactobacillus rhamnosus* strain. In particular, the present invention relates to a composition comprising a *Lactobacillus rhamnosus* optionally in combination with a further lactobacilli and the use of the same in the treatment, prevention or alleviation of candidiasis.

BACKGROUND OF THE INVENTION

*Candida* species are commensals in the oral cavity being part of the normal microbiota in around 50% of healthy individuals. Nevertheless, *Candida* species are opportunistic pathogens, which under certain circumstances cause infection in the oral mucosa, termed oral candidiasis. Infections are primarily caused by *Candida albicans* that has the ability to switch between the blastospore form and the more invasive hyphae form. However, other *Candida* species have been isolated from infected sites in the oral cavity, including *C. glabrata, C. krusei, C. tropicalis, C. dubliniensis*, and *C. parapsilosis*.

Currently, an increase in fungal resistance to antimycotic therapy causes concern and consequently, an alternative bio-ecological approach of fungal management has been proposed.

There is growing interest of probiotic bacteria to prevent and combat oral diseases. Probiotic bacteria are defined by the WHO as "Live microorganism that, when administered in adequate amounts, confer a health benefit on the host". The most common probiotic genera *Bifidobacterium* and *Lactobacillus* are believed to act by competitive exclusion of pathogens from the oral mucosal adhesion sites, by competing for available nutrients, and by altering the mucosal immune host defence.

In addition, some probiotic bacteria produce acids from carbohydrate fermentation rendering a low pH, and some lactic acid bacteria produce hydrogen peroxide ($H_2O_2$) and bacteriocins which are harmful to pathogens.

Probiotic bacteria are considered beneficial in several areas of the human body, including the oral cavity and vagina. Thus, a healthy microbiota may prevent the development of pathogenic infections, such as pathogenic *Candida* infection.

Candidiasis is an infection caused by a species of *Candida. Candida* appears in the normal healthy microbiota of the skin and inside the body, in places such as the mouth, throat, gut, and vagina, without being pathogenic. Occasionally, *Candida* can cause a pathogenic infection if the environment inside the mouth, throat, or esophagus changes in a way that encourages the growth of the fungi.

Candidiasis in the mouth and throat is referred to as thrush or oropharyngeal candidiasis. Candidiasis in the esophagus is referred to as esophageal candidiasis or *Candida* esophagitis. Esophageal candidiasis is one of the most common infections in people living with HIV/AIDS.

Candidal vulvovaginitis is caused by inflammatory changes in the vaginal and vulvar epithelium secondary to infection with *Candida* species, most commonly *Candida albicans. Candida* is part of the normal vaginal microbiota in many women and is often asymptomatic. Therefore, candidal vulvovaginitis develops when *Candida* is causing a pathogenic infection in the vagina/vulva, which is associated with symptoms of irritation, itching, dysuria, or inflammation.

Consequently, there is a need for compositions that contributes to the maintenance of oral or vaginal health. In particular, there is a need for compositions that may be used in the treatment, prevention or alleviation of candidiasis.

SUMMARY OF THE INVENTION

The present invention was made in view of the prior art described above, and the object of the present invention is to provide a probiotic composition, which may be used in the maintenance of oral health or vaginal health. In particular, in the object of the present invention is to provide a probiotic composition for use in the treatment, prevention or alleviation of candidiasis.

To solve the problem, the present invention provides compositions comprising *Lactobacillus rhamnosus* strain ERB 36 (DSM 32992) and methods of using the same. That is, the inventors of the present invention have found that the composition of the present invention comprising *Lactobacillus rhamnosus* strain ERB 36 (DSM 32992) is capable of inhibiting the growth species of *Candida* known to be associated with pathogenic oral or vaginal infections.

Zheng et al. recently proposed taxonomic amendments to the genus *Lactobacillus*. (Zheng et al. (2020), incorporated herein by reference). However, the proposed taxonomic changes have not been approved and implemented at present. The suggested taxonomic changes that may become relevant to the present invention are Lacticaseibacillus *rhamnosus* (currently *Lactobacillus rhamnosus*) and Latilactobacillus *curvatus* (*Lactobacillus curvatus*).

A first aspect of the present invention provides *Lactobacillus rhamnosus* strain ERB 36 (DSM 32992).

In a second aspect, the present invention provides a culture comprising *Lactobacillus rhamnosus* strain ERB 36 (DSM 32992).

In a third aspect, the present invention provides a composition comprising *Lactobacillus rhamnosus* strain ERB 36 (DSM 32992).

A fourth aspect of the present invention relates to the composition according to the present invention for use as a medicament.

A fifth aspect of the present invention relates to the composition according to the present invention for use in the treatment, prevention or alleviation of candidiasis.

In a sixth aspect, the present invention provides a nutraceutical comprising the composition according to the present invention.

A further aspect of the present invention relates to a nutritional supplement comprising the composition according to the present invention.

In a further aspect, the present invention provides a container containing the composition according to the present invention.

In a related aspect, the present invention provides a kit comprising a plurality of containers according to the present invention.

A further aspect of the present invention relates to a method for reducing a *Candida* spp. infection in a subject, said method comprising the step of providing a therapeutic effective amount of a composition according to the present invention to a subject in the need thereof.

Yet a further aspect of the present invention relates to a method for reducing, alleviating or preventing candidiasis in a subject, said method comprising the step of providing a therapeutic effective amount of a composition according to the present invention to a subject in the need thereof.

A related aspect of the present invention provides a method for maintenance of oral health or vaginal health in a subject, said method comprising the step of providing a therapeutic effective amount of a composition according to the present invention to a subject in the need thereof.

Figure 1:
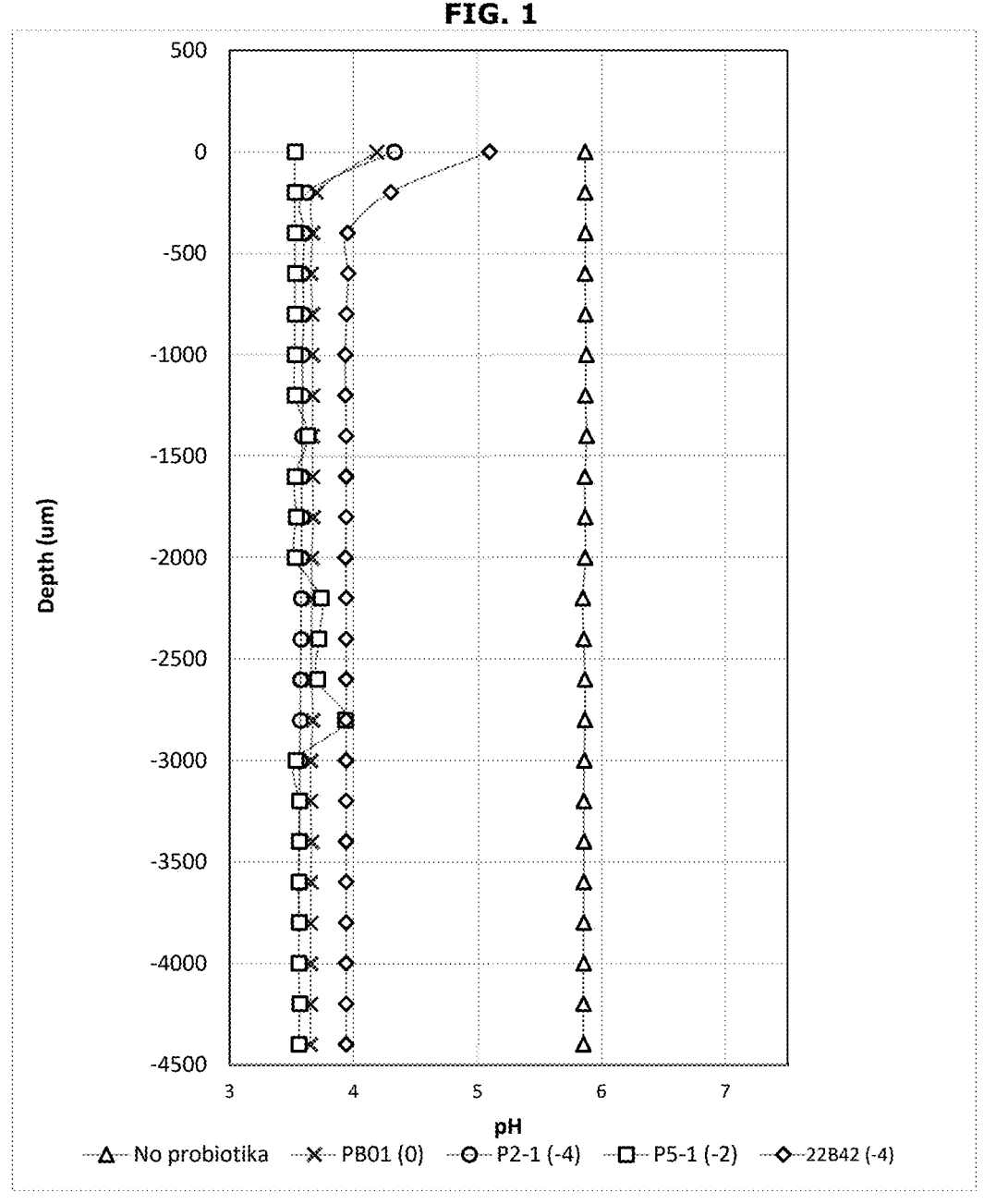
FIG. 1 pH measurements in control agar plates without *Candida*.

Table 1 List of microbes used in the Example 1.

Table 2 Growth inhibition of six clinical isolates and six reference *Candida* species by 14 different lactobacilli strains at different cell concentrations (colony forming units (CFU)/ ml). Median inhibition scores according to a modified Simark-Mattson et al., 2007 scoring system: 0=complete inhibition (no visible colonies); 1=almost total inhibition (colonies are slightly visible); 2=slight inhibition (colonies are clearly visible but smaller than at the control plate); 3=no growth inhibition (colonies equal to those at the control plate)

Table 3 Frequency in percent (%) of growth inhibition score 0-3 for each lactobacilli strain (all concentrations).

Table 4 4×4 table displaying the comparison between the four best performing lactobacilli. Numbers indicating p-values. Chi-squared test between the selected four lactobacilli strains.

Table 5 Frequency in percent (%) of growth inhibition score 0-3 for each dose based on tests with all 14 lactobacilli strains.

Table 6 Frequency in percent (%) of growth inhibition score 0-3 for each *Candida* spp. based on tests with all 14 lactobacilli strains (all concentrations).

DETAILED DESCRIPTION OF THE INVENTION

An object of the present invention is to provide a probiotic composition for use in the treatment, prevention or alleviation of candidiasis. In order to identify bacteria capable of inhibiting the growth of *Candida* spp., the inventors conducted an agar overlay interference study employing 14 lactobacilli strains and six *Candida* spp. (see Example 1).

The *Lactobacillus rhamnosus* strain ERB 36 (DSM 32992) and *Lactobacillus rhamnosus* strain ERB18 (DSM 32991) included in the study was isolated from the oral mucosa of a healthy child donor. The study identified the two strains of *Lactobacillus* as having particular inhibitory effects on the growth of the *Candida* spp.

A further study revealed that *Lactobacillus rhamnosus* strain ERB 36 (DSM 32992) and *Lactobacillus rhamnosus* strain ERB18 (DSM 32991) as the best performing lactobacilli with respect to acid production suggesting that the acid production plays an important role in growth inhibition of *Candida* spp. (see Example 2).

*Lactobacillus rhamnosus* ERB 36 (also referred to as P5-1 herein) was deposited with DSMZ-Deutsche Sammlung von Mikroorganismen und Zellkulturen GmbH (Inhoffenstr. 7 B, D-38124 Braunschweig, Germany) on 12 Dec. 2018 for the purposes of patent deposit according to the Budapest Treaty. The deposit number of *Lactobacillus rhamnosus* strain ERB 36 is DSM 32992.

*Lactobacillus rhamnosus* ERB18 (also referred to as P2-1 herein) was deposited with DSMZ-Deutsche Sammlung von Mikroorganismen und Zellkulturen GmbH (Inhoffenstr. 7 B, D-38124 Braunschweig, Germany) on 12 Dec. 2018 for the purposes of patent deposit according to the Budapest Treaty. The deposit number of *Lactobacillus rhamnosus* strain ERB18 is DSM 32991.

A first aspect of the present invention provides *Lactobacillus rhamnosus* strain ERB 36 (DSM 32992). The strain is also referred to as P5-1 herein and was identified as being superior over the other strains included in the study (see Example 1 and 2).

In one embodiment, the isolated *Lactobacillus rhamnosus* strain ERB 36 (DSM 32992) is provided in its pure isolated form. In another embodiment, the *Lactobacillus rhamnosus* strain ERB 36 (DSM 32992) is provided in an essential isolated form.

Microbial Culture, Culture Broth

A second aspect of the present invention provides a microbial culture, culture broth or ferment comprising the *Lactobacillus rhamnosus* strain ERB 36 (DSM 32992) of the present invention. The *Lactobacillus rhamnosus* strain ERB 36 (DSM 32992) cells comprised in the microbial culture, culture broth or ferment are initially essentially all viable. By essentially all viable means that at least 50% of the bacteria present in microbial culture, culture broth or ferment immediately after the preparation of the same are viable, such as at least 75%, for example at least 85%, such as at least 90%, for example at least 95%.

The viability of the bacteria may be confirmed by plating the bacteria on a suitable medium (e.g. solidified agar in a standard sized Petri dish) and determine the number of colonies formed. The measure, colony forming unit (or CFU), is used to quantify the amount of viable (live) bacteria in the composition (reflecting the capacity of the bacteria to replicate).

The bacteria comprised in the microbial culture, culture broth, ferment and composition of the present invention confers a health benefit to the subject, when ingested in adequate amounts by a subject (such as in the form of a formulation as described herein). It follows that the bacteria is non-pathogenic and does not confer any harmful effect in the ingested amounts. The bacteria are also referred to as probiotic bacteria.

In one embodiment of the present invention, the microbial culture, culture broth or ferment is a pure or essentially pure, in the sense that the only or essentially only organism present is *Lactobacillus rhamnosus* strain ERB 36 (DSM 32992).

In another embodiment, the microbial culture, culture broth or ferment comprises at least one further probiotic microorganism, preferably a probiotic bacterium. Preferably, the at least further probiotic bacterium is a lactobacilli sp.

In another embodiment, the microbial culture, culture broth or ferment comprises at least one lactobacilli sp. selected from the group consisting of *Lactobacillus rhamnosus* strain ERB18 (DSM 32991), *Lactobacillus jensenii* 22B42, *Lactobacillus rhamnosus* strain PB01 (DSM 14870) and *Lactobacillus curvatus* EB10 (DSM 32307).

In a preferred embodiment, the microbial culture, culture broth or ferment further comprises *Lactobacillus rhamnosus* strain ERB18 (DSM 32991). In a further embodiment, the bacteria present in the microbial culture, culture broth or ferment further comprises or consists essentially of *Lactobacillus rhamnosus* strain ERB 36 (DSM 32992) and at least one lactobacilli sp. selected from the group consisting of *Lactobacillus rhamnosus* strain ERB18 (DSM 32991), *Lactobacillus jensenii* 22B42, *Lactobacillus rhamnosus* strain PB01 (DSM 14870) and *Lactobacillus curvatus* EB10 (DSM 32307)

The microbes present in the microbial culture, culture broth or ferment are preferably balanced such that *Lactobacillus rhamnosus* strain ERB 36 (DSM 32992) is not outnumbered by other bacteria included in the microbial culture, culture broth or ferment. For example, the CFU in the microbial culture, culture broth or ferment may be evenly distributed between the microbes present.

In another embodiment, at least 50% of CFU is *Lactobacillus rhamnosus* strain ERB 36 (DSM 32992), such as at least 60%, for example at least 70%, such as at least 80%, for example at least 90%, such as at least 95% of CFU is *Lactobacillus rhamnosus* strain ERB 36 (DSM 32992).

In a further embodiment, about 50% of CFU is *Lactobacillus rhamnosus* strain ERB 36 (DSM 32992) and about 50% of CFU is *Lactobacillus rhamnosus* strain ERB18 (DSM 32991).

In yet a further embodiment, about 50% of CFU is *Lactobacillus rhamnosus* strain ERB 36 (DSM 32992) and about 50% of CFU is *Lactobacillus jensenii* 22B42.

In yet a further embodiment, about 50% of CFU is *Lactobacillus rhamnosus* strain ERB 36 (DSM 32992) and about 50% of CFU is *Lactobacillus rhamnosus* strain PB01 (DSM 14870).

In yet a further embodiment, about 50% of CFU is *Lactobacillus rhamnosus* strain ERB 36 (DSM 32992) and about 50% of CFU is *Lactobacillus curvatus* strain EB10 (DSM 32307).

Composition

A third aspect provides a composition comprising *Lactobacillus rhamnosus* strain ERB 36 (DSM 32992). In one embodiment of the present invention, the composition is a pure or essentially pure, in the sense that the only or essentially only organism present is *Lactobacillus rhamnosus* strain ERB 36 (DSM 32992).

In another embodiment, the composition comprises at least one further probiotic microorganism, preferably a probiotic bacterium. In one embodiment of the present invention, the composition is a pure or essentially pure, in the sense that the only or essentially only organism present is *Lactobacillus rhamnosus* strain ERB 36 (DSM 32992).

In another embodiment, the composition comprises at least one further probiotic microorganism, preferably a probiotic bacterium. In one embodiment, the composition further comprises *Bacillus subtilis* DE111. Preferably, the at least further probiotic bacterium is a lactobacilli sp.

In another embodiment, the composition further comprises at least one *Lactobacillus* sp. selected from the group consisting of *Lactobacillus rhamnosus* strain ERB18 (DSM 32991), *Lactobacillus jensenii* 22B42, *Lactobacillus rhamnosus* strain PB01 (DSM 14870) and *Lactobacillus curvatus* EB10 (DSM 32307).

In a preferred embodiment, the composition further comprises *Lactobacillus rhamnosus* strain ERB18 (DSM 32991). In a further embodiment, the bacteria present in the microbial culture, culture broth or ferment further comprises, consists or consists essentially of *Lactobacillus rhamnosus* strain ERB 36 (DSM 32992) and at least one lactobacilli sp. selected from the group consisting of *Lactobacillus rhamnosus* strain ERB18 (DSM 32991), *Lactobacillus jensenii* 22B42, *Lactobacillus rhamnosus* strain PB01 (DSM 14870) and *Lactobacillus curvatus* EB10 (DSM 32307).

The microbes present in the composition are preferably balanced such that *Lactobacillus rhamnosus* strain ERB 36 (DSM 32992) is not outnumbered by other bacteria included in the microbial culture, culture broth or ferment. For example, the CFU in the microbial culture, culture broth or ferment may be evenly distributed between the microbes present.

In another embodiment, at least 50% of CFU present in the composition is *Lactobacillus rhamnosus* strain ERB 36 (DSM 32992), such as at least 60%, for example at least 70%, such as at least 80%, for example at least 90%, such as at least 95% of CFU is *Lactobacillus rhamnosus* strain ERB 36 (DSM 32992).

In a further embodiment, about 50% of CFU present in the composition is *Lactobacillus rhamnosus* strain ERB 36 (DSM 32992) and about 50% of CFU is *Lactobacillus rhamnosus* strain ERB18 (DSM 32991).

In yet a further embodiment, about 50% of CFU present in the composition is *Lactobacillus rhamnosus* strain ERB 36 (DSM 32992) and about 50% of CFU is *Lactobacillus jensenii* 22B42.

In yet a further embodiment, about 50% of CFU present in the composition is *Lactobacillus rhamnosus* strain ERB 36 (DSM 32992) and about 50% of CFU is *Lactobacillus rhamnosus* strain PB01 (DSM 14870).

In yet a further embodiment, about 50% of CFU present in the composition is *Lactobacillus rhamnosus* strain ERB 36 (DSM 32992) and about 50% of CFU is *Lactobacillus curvatus* strain EB10 (DSM 32307).

The initial colony forming units (CFU) and the continued stability and viability of the composition is influenced by a variety of factors. The stability of a probiotic composition tested at the time of manufacture will depend on a combination of factors. Variations in packaging, temperature, and humidity will affect the viability of probiotic products before they are taken. Protective factors that help to preserve the freshness and viability of the probiotic strains in a supplement include refrigeration, resistant packaging, and storage in a cool, dry place. If a probiotic composition is held in conditions that are very warm or moist, the CFU in the composition declines. Thus, the continued stability and viability is dependent on limiting their exposure to stimulating environmental conditions such as warmth and moisture.

In one embodiment of the present invention, the composition comprises at least $10^5$ CFU of lactobacilli per gram of said composition, such as at least $10^6$ CFU of lactobacilli per gram of said composition, for example at least $10^7$ CFU of lactobacilli per gram of said composition, such as at least $10^8$ CFU of lactobacilli per gram of said composition, for example at least $10^9$ CFU of lactobacilli per gram of said composition, such as at least $10^{10}$ CFU of lactobacilli per gram of said composition.

In one embodiment, the composition of *Lactobacillus rhamnosus* strain ERB 36 (DSM 32992), for example at least $10^7$ CFU *Lactobacillus rhamnosus* strain ERB 36 (DSM 32992) per gram of said composition, such as at least $10^8$ CFU *Lactobacillus rhamnosus* strain ERB 36 (DSM 32992) per gram of said composition, for example at least $10^9$ CFU *Lactobacillus rhamnosus* strain ERB 36 (DSM 32992) per gram of said composition, such as at least $10^{10}$ CFU *Lactobacillus rhamnosus* strain ERB 36 (DSM 32992) per gram of said composition.

In one embodiment of the present invention, the composition comprises from $10^5$ to $10^{13}$ CFU of lactobacilli per gram of said composition, such as $10^5$ to $10^{13}$ CFU of *Lactobacillus rhamnosus* strain ERB 36 (DSM 32992). In another embodiment of the present invention, the composition comprises from $10^6$ to $10^{12}$ CFU of lactobacilli per gram of said composition, such as $10^6$ to $10^{12}$ CFU of *Lactobacillus rhamnosus* strain ERB 36 (DSM 32992). In yet another embodiment, the composition comprises from $10^7$ to $10^{11}$ CFU of lactobacilli per gram of said composition, such as $10^7$ to $10^{11}$ CFU of *Lactobacillus rhamnosus* strain ERB36 (DSM 32992). In a further embodiment, the composition comprises from $10^8$ to $10^{10}$ CFU of lactobacilli per gram of said composition, such as $10^8$ to $10^{10}$ CFU of *Lactobacillus rhamnosus* strain ERB36 (DSM 32992), for example $10^9$ lactobacilli per gram of said composition.

In one embodiment, the composition comprises *Lactobacillus rhamnosus* strain ERB36 (DSM 32992) and *Lactobacillus rhamnosus* strain ERB18 (DSM 32991).

In a further embodiment, the composition further comprises at least $10^7$ CFU *Lactobacillus rhamnosus* strain ERB18 (DSM 32991) per gram of said composition, such as at least $10^8$ CFU *Lactobacillus rhamnosus* strain ERB18 (DSM 32991) per gram of said composition, for example at least $10^9$ CFU *Lactobacillus rhamnosus* strain ERB18 (DSM 32991) per gram of said composition, such as at least $10^{10}$ CFU *Lactobacillus rhamnosus* strain ERB18 (DSM 32991) per gram of said composition.

In one embodiment, the composition comprises *Lactobacillus rhamnosus* strain ERB 36 (DSM 32992) and *Lactobacillus jensenii* 22B42.

In a further embodiment, the composition further comprises at least $10^7$ CFU of *Lactobacillus jensenii* 22B42 per gram of said composition, such as at least $10^8$ CFU *Lactobacillus jensenii* 22B42 per gram of said composition, for example at least $10^9$ CFU *Lactobacillus jensenii* 22B42 per gram of said composition, such as at least $10^{10}$ CFU *Lactobacillus jensenii* 22B42 per gram of said composition.

In one embodiment, the composition comprises *Lactobacillus rhamnosus* strain ERB 36 (DSM 32992) and *Lactobacillus rhamnosus* strain PB01 (DSM 14870).

In a further embodiment, the composition further comprises at least $10^7$ CFU of *Lactobacillus rhamnosus* strain PB01 (DSM 14870) per gram of said composition, such as at least $10^8$ CFU *Lactobacillus rhamnosus* strain PB01 (DSM 14870) per gram of said composition, for example at least $10^9$ CFU *Lactobacillus rhamnosus* strain PB01 (DSM 14870) per gram of said composition, such as at least $10^{10}$ *Lactobacillus rhamnosus* strain PB01 (DSM 14870) per gram of said composition.

In one embodiment, the composition comprises *Lactobacillus rhamnosus* strain ERB 36 (DSM 32992) and *Lactobacillus curvatus* EB10 (DSM 32307).

In a further embodiment, the composition further comprises at least $10^7$ CFU of *Lactobacillus curvatus* EB10 (DSM 32307) per gram of said composition, such as at least $10^8$ CFU *Lactobacillus curvatus* EB10 (DSM 32307) per gram of said composition, for example at least $10^9$ CFU *Lactobacillus curvatus* EB10 (DSM 32307) per gram of said composition, such as at least $10^{10}$ *Lactobacillus curvatus* EB10 (DSM 32307) per gram of said composition.

The lactobacilli strains of the composition of the present invention may be provided in any suitable form depending on the formulation of the composition. In a preferred embodiment, the lactobacilli is in a lyophilized, spray dried, vacuum dried or microencapsulated form or any combination thereof. Thus, in one embodiment, the composition of the invention is provided in a container, such as a vial, comprising lactobacilli strain(s) in lyophilized or spray dried form.

Excipients

In one embodiment of the present invention, the composition further comprises at least one excipient. In another embodiment, the at least one excipient is selected from the group consisting of a bulking agent, a binder, a glazing agent, a sweetener and a flavour.

In the context of the present invention, the term "bulking agent" refers to an additive that increases the volume or weight of the composition while keeping its utility or functionality intact. In one embodiment of the present invention, the composition comprises at least one bulking agent selected from the group consisting of xylitol, sorbitol, erythritol, maltitol, lactitol, inositol and mannitol microcrystalline cellulose, glucose, isomalt and starch, such as potato starch or corn starch.

In the context of the present invention, the term "binder" refers to binding material that keeps components of the composition together, stabilizes a form or shape, or causes a mixture to coalesce. In one embodiment of the present invention, the composition comprises at least one binder selected from the group consisting of maltodextrin and sodium carboxymethylcellulose.

In the context of the present invention, the term "glazing agent" refers to a natural or synthetic substance that provides a waxy, homogeneous, coating to provide protection to the composition. In one embodiment of the present invention, the composition comprises at least one glazing agent selected from the group consisting of mono- and diglyceride of fatty acids, silicon dioxide, stearic acid, beeswax, candelilla wax, carnauba wax, shellac, microcrystalline wax, crystalline wax, lanolin, oxidized polyethylene wax, esters of colophonium, paraffin.

The composition of the present invention may further comprise at least one sweetener. In one embodiment, the at least one sweetener is a low calorie sweetener.

In one embodiment, the low calorie sweetener is selected from the list consisting of a bulk sweetener and an intense sweetener. In yet an embodiment, the low calorie sweetener is a sugar alcohol. In a further embodiment, the low calorie sweetener is selected from the list consisting of xylitol, sorbitol, erythritol, maltitol, lactitol, isomalt, inositol and mannitol.

The composition may comprise a combination of low calorie sweetener such as a combination of sugar alcohols as described above. Alternatively, the composition may also comprise a combination of one or more bulk sweetener and one or more intense sweeteners.

In one embodiment, the composition comprises an intense sweetener selected from the list consisting of saccharin, aspartame, *stevia*, a steviol glycoside such as stevioside, sucralose and acesulfame such as acesulfame potassium (Ace-K). In another embodiment, the sweetener is selected from the group consisting of rebaudioside, aspartame, neotame, saccharin, and advantame.

The composition of the present invention comprises at least one flavour. More than one flavour may be included to provide a more complex tasting experience. In one embodiment, said at least one flavour is at least one flavour selected from the group consisting of citric acid, lemon flavour, honeydew melon flavour, blueberry flavour, peach flavour, strawberry flavour, raspberry flavour, cola flavour, chocolate flavour, peppermint flavour, cherry flavour, lime flavour, orange flavour, vanilla flavour, tangerine flavour, liquorice flavour, apricot flavour, eucalyptus flavour, green tea flavour, ginger flavour and bilberry flavour. The amount of flavour compounds in the composition may vary. In one embodiment, the at least one flavour is present in an amount from 1 to 10% w/w in said composition.

In a preferred embodiment, the composition of the invention comprises:

(i) bulking agents in the form of xylitol and microcrystalline cellulose, isomalt, (ii) binders in the form of maltodextrin and sodium carboxymethylcellulose, (iii) glazing agents in the form of mono- and diglyceride of fatty acids and silicon dioxide, (iv) a sweetener in the form of steviol glycoside, and (v) optionally flavours e.g. in the form of citric acid and lemon flavour.

The composition may also comprise a prebiotic that stimulates the proliferation of the microorganism in the gastrointestinal (GI) tract of the subject ingesting the composition. In one embodiment, the composition further comprises at least one prebiotic selected from the group consisting of sialo-oligosaccharides (SOS), fructo-oligosaccharides (FOS), galacto-oligosaccharides (GOS), isomalto-oligosaccharides (IMO), xylo-oligosaccharides (XOS), arabino-xylo oligosaccharides (AXOS), mannan oligosaccharides (MOS), oligosaccharides of soy, glycosylsucrose (GS), lactosucrose (LS), sialyl-lactose (SL) Fucosyl-lactose (FL), Lacto-N-Neotetraose (LNNT), lactulose (LA), palatinose-oligosaccharides (PAO), malto-oligosaccharides, gums and/or hydrolysates thereof, pectins, starches, and/or hydrolysates thereof.

Formulation of the Composition of the Invention

The composition may be provided in any suitable formulation. Preferably, the composition is provided in a formulation suitable for oral administration. In another embodiment, the composition is provided in a formulation suitable for vaginal administration. In one embodiment, the composition is in the form of a tablet, a capsule, powder, effervescent tablet, effervescent powder, granulate, a lyophilized product, a spray dried product, a vacuum dried product, a microencapsulated product, a suspension, spray, a gel or a cream or any combination thereof. In a preferred embodiment, the composition is formulated as a tablet, preferably a chewable tablet.

In one embodiment, the composition of the present invention is formulated as a pharmaceutical composition, which comprises at least one pharmaceutically acceptable excipient or carrier.

Use of the Composition of the Present Invention

One aspect of the present invention provides the composition for use as a medicament. The inventor has discovered that the composition can inhibit the growth of *Candida* spp., which are known to cause pathogenic oral and vaginal infection.

Thus, an aspect of the present invention relates to the composition of the present invention for use in the treatment of an inflammatory condition. In one embodiment, the said inflammatory disease is an inflammatory condition in oral cavity or in the vagina. In one embodiment, the composition for use in the treatment of a pathogenic *Candida* infection, for example in oral cavity or the vagina.

In a preferred embodiment, the composition of the invention is for use in the treatment, prevention or alleviation of candidiasis, such as oral candidiasis or vaginal candidiasisis.

The infectious *Candida* spp. may be any *Candida* spp. In one embodiment, the *Candida* spp. is selected from the list consisting of *Candida glabrata, Candida krusei, Candida tropicalis, Candida dubliniensis, Candida parapsilosis*, and *Candida albicans*. In a preferred embodiment, the composition is for use in a pathogenic *Candida* infection with the proviso that said candidiasis is not caused by *Candida albicans*.

The composition may be for administration as a once daily dose. The composition may thus be formulated accordingly, e.g. as a one daily dose unit. The composition may also be for administration as a twice daily dose, three times daily dose or even for administration several times daily. It follows that the composition may thus be formulated according to the dosage regimen. In one embodiment of the present invention, the composition is administrated twice daily.

In one embodiment, the composition comprises at least $10^7$ CFU lactobacilli per daily dose, such as in the range of $10^7$ to $10^{10}$ CFU lactobacilli per daily dose, such as $10^8$ to $10^9$ CFU lactobacilli per daily dose.

In one embodiment, the composition comprises at least $10^7$ CFU *Lactobacillus rhamnosus* strain ERB 36 (DSM 32992) per daily dose, for example at least $5\times10^7$ CFU *Lactobacillus rhamnosus* strain ERB 36 (DSM 32992) per daily dose, such as in the range of $10^7$ to $10^{10}$ CFU *Lactobacillus rhamnosus* strain ERB 36 (DSM 32992) per daily dose, such as $10^8$ to $10^9$ CFU *Lactobacillus rhamnosus* strain ERB 36 (DSM 32992) per daily dose.

In another embodiment, the composition further comprises *Lactobacillus rhamnosus* strain ERB18 (DSM 32991). In one embodiment, the composition further comprises at least $10^7$ CFU *Lactobacillus rhamnosus* strain ERB18 (DSM 32991) per daily dose, for example at least $5\times10^7$ CFU *Lactobacillus rhamnosus* strain ERB18 (DSM 32991) per daily dose, such as in the range of $10^7$ to $10^{10}$ CFU *Lactobacillus rhamnosus* strain ERB18 (DSM 32991) per daily dose, such as $10^8$ to $10^9$ CFU *Lactobacillus rhamnosus* strain ERB18 (DSM 32991) per daily dose.

In one embodiment, the composition comprises at least $10^7$ CFU *Lactobacillus rhamnosus* strain ERB 36 (DSM 32992) per daily dose, such as at least $5\times10^7$ CFU *Lactobacillus rhamnosus* strain ERB 36 (DSM 32992) per daily dose and at least $1\times10^7$ *Lactobacillus rhamnosus* strain ERB 18 (DSM 32991) per daily dose, such as at least $5\times10^7$ CFU *Lactobacillus rhamnosus* strain ERB 18 (DSM 32991) per daily dose.

In one embodiment, the composition comprises at least $10^7$ CFU *Lactobacillus rhamnosus* strain ERB 36 (DSM 32992) per daily dose, such as at least $5\times10^7$ CFU *Lactobacillus rhamnosus* strain ERB 36 (DSM 32992) per daily dose and at least $1\times10^7$ *Lactobacillus jensenii* 22B42 per daily dose, such as at least $5\times10^7$ CFU *Lactobacillus jensenii* 22B42 per daily dose.

In one embodiment, the composition comprises at least $10^7$ CFU *Lactobacillus rhamnosus* strain ERB 36 (DSM 32992) per daily dose, such as at least $5\times10^7$ CFU *Lactobacillus rhamnosus* strain ERB 36 (DSM 32992) per daily dose and at least $1\times10^7$ *Lactobacillus rhamnosus* strain PB01 (DSM 14870) per daily dose, such as at least $5\times10^7$ CFU *Lactobacillus rhamnosus* strain PB01 (DSM 14870) per daily dose.

In one embodiment, the composition comprises at least $10^7$ CFU *Lactobacillus rhamnosus* strain ERB 36 (DSM 32992) per daily dose, such as at least $5\times10^7$ CFU *Lactobacillus rhamnosus* strain ERB 36 (DSM 32992) per daily dose and at least $1\times10^7$ *Lactobacillus curvatus* EB10 (DSM 32307) per daily dose, such as at least $5\times10^7$ CFU *Lactobacillus curvatus* EB10 (DSM 32307) per daily dose.

In one embodiment of the present invention, the composition for the use according to the present invention is administrated orally. For this purpose, the composition may be provided in the form of a tablet, a capsule, powder, effervescent tablet, effervescent powder, granulate, a micro-encapsulated product, a suspension, spray, a gel or a cream. In a preferred embodiment, the composition is formulated as a tablet, preferably a chewable tablet.

One aspect of the present invention concerns a method for maintenance of oral health or vaginal health in a subject, said method comprising the step of providing a therapeutic effective amount of a composition according to the present invention to a subject in the need thereof.

Another aspect of the present invention provides a method for reducing a *Candida* spp. infection in a subject, said method comprising the step of providing a therapeutic effective amount of a composition according to present invention to a subject in the need thereof.

In a further aspect, the invention provides a method for reducing, alleviating or preventing candidiasis in a subject, said method comprising the step of providing a therapeutic effective amount of a composition according to present invention to a subject in the need thereof.

In one embodiment, the candidiasis is oral candidiasis. In another embodiment, the candidiasis is vaginal candidiasis.

The infectious *Candida* spp. may be any *Candida* spp. In one embodiment, the *Candida* spp. is selected from the list consisting of *Candida glabrata, Candida krusei, Candida tropicalis, Candida dubliniensis, Candida parapsilosis*, and *Candida albicans*. In a preferred embodiment, the composition is for use in a pathogenic *Candida* infection with the proviso that said candidiasis is not caused by *Candida albicans*.

The above methods preferably comprise daily administration of the composition of the present invention. In one embodiment, the composition provided to the subject comprises at least $10^7$ CFU lactobacilli per daily dose, such as in the range of $10^7$ to $10^{10}$ CFU lactobacilli per daily dose, such as $10^8$ to $10^9$ CFU lactobacilli per daily dose.

In one embodiment, the composition comprises at least $10^7$ CFU *Lactobacillus rhamnosus* strain ERB 36 (DSM 32992) per daily dose, for example at least $5\times10^7$ CFU *Lactobacillus rhamnosus* strain ERB 36 (DSM 32992) per daily dose, such as in the range of $10^7$ to $10^{10}$ CFU *Lactobacillus rhamnosus* strain ERB 36 (DSM 32992) per daily dose, such as $10^8$ to $10^9$ CFU *Lactobacillus rhamnosus* strain ERB 36 (DSM 32992) per daily dose.

Nutraceutical Composition and Nutritional Supplement

In the context of the present invention a nutritional supplement (or a dietary supplement) is a product intended for ingestion that contains a "dietary ingredient" intended to add further nutritional value to (supplement) the diet.

One aspect of the present invention provides a nutritional supplement comprising the composition of the present invention.

In the context of the present invention, the term "nutraceuticals" refers to a product derived from food sources with the extra health benefits described herein in addition to the basic nutritional value found in foods. The nutraceuticals of the present invention may contribute to the maintenance of oral or vaginal health in a subject and reduce the risk of obtaining an inflammatory condition in the mouth cavity, such as a periodontal disease, for example gingivitis. The nutraceuticals of the present invention may also reduce the risk of obtaining pathogenic infections of *Candida* species.

One aspect of the present invention provides a nutraceutical comprising the composition of the present invention. In one embodiment, the nutraceutical is provided in the form of a functional food. Functional food is a category which includes whole foods and fortified with the composition of the present invention. In another embodiment, the nutraceutical is provided in the form of a medical food. The medical food is formulated to be consumed or administered internally, under the supervision of a qualified physician.

The nutritional supplement may be provided in many forms such as tablets (such as chewable tablet), effervescent tablet, effervescent powder, capsules, softgels, gelcaps, liquids, or powders.

The nutritional and nutraceutical supplement of the present invention may contribute to the maintenance of oral or vaginal health in a subject and reduce the risk of obtaining pathogenic infections of *Candida* species.

Packaging

The composition of the present invention is typically filled in a container, which is preferably sealed, which provide an oxygen and moisture barrier in order to maintain the integrity of the composition.

Accordingly, one aspect of the present invention concerns a container containing the composition of the present invention. Non limiting examples of suitable containers include a blister pack (such as a blister pack of tablets), a stick, bag, pouch or capsule. In a preferred embodiment, the container is an aluminium foil or a polyethylene stick, which is typically sealed by welding. The stick is typically configured for easy tear opening. The stick may have a tear notch. Thus, the stick may be discarded after ingestion of the composition. Preferably, the container, such as in the form of a stick or blister pack of tablets, comprises a single dose of the composition.

The container may comprise desiccant to that induces or sustains a state of dryness (desiccation) of the composition. The desiccants may be in forms other than solid, and may work through other principles, such as chemical bonding of water molecules.

The desiccant may be any desiccant suitable for food or pharmaceutical applications. Examples of desiccant include silica, charcoal and molecular sieves.

In a further aspect of the present invention, a kit is provided, wherein said kit comprises a plurality of containers each comprising the composition of the present invention. Preferably, each container of the kit comprises a single dose of the composition. Every container of the kit may comprise the same composition. Alternatively, the containers may comprise different compositions, e.g. the compositions may comprise different flavours.

The invention is further described in the following non-limiting embodiments:

Embodiment 1. *Lactobacillus rhamnosus* strain ERB 36 (DSM 32992).

Embodiment 2. A culture comprising *Lactobacillus rhamnosus* strain ERB 36 (DSM 32992).

Embodiment 3. The culture according to embodiment 2 comprising at least one further lactobacilli sp.

Embodiment 4. The culture according to embodiment 2 or 3 further comprising *Lactobacillus rhamnosus* strain ERB18 (DSM 32991), *Lactobacillus rhamnosus* strain PB01 (DSM 14870) and/or *Lactobacillus curvatus* EB10 (DSM 32307).

Embodiment 5. A composition comprising *Lactobacillus rhamnosus* strain ERB 36 (DSM 32992).

Embodiment 6. The composition according to embodiment 5 comprising at least one further lactobacilli sp.

Embodiment 7. The composition according to embodiment 5 or 6 further comprising *Lactobacillus rhamnosus* strain ERB18 (DSM 32991), *Lactobacillus rhamnosus* strain PB01 (DSM 14870) and/or *Lactobacillus curvatus* EB10 (DSM 32307).

Embodiment 8. The composition according to embodiment 6 or 7, wherein said composition comprises from $10^5$ to $10^{13}$ CFU of lactobacilli per gram of said composition.

Embodiment 9. The composition according to any one of embodiments 5 to 8, wherein said composition comprises from $10^6$ to $10^{12}$ CFU of lactobacilli per gram of said composition.

Embodiment 10. The composition according to any one of embodiments 5 to 9, wherein said composition comprises from $10^7$ to $10^{11}$ CFU of lactobacilli per gram of said composition.

Embodiment 11. The composition according to any one of embodiments 5 to 10, wherein said composition comprises from $10^8$ to $10^{10}$ CFU of lactobacilli per gram of said composition, such as $10^9$ lactobacilli per gram of said composition.

Embodiment 12. The composition according to embodiment 11 comprising at least $10^7$ CFU *Lactobacillus rhamnosus* strain ERB 36 (DSM 32992) per gram of said composition.

Embodiment 13. The composition according to any one of the preceding embodiments, wherein said lactobacilli is in a lyophilized or spray dried form.

Embodiment 14. The composition according to any one of the preceding embodiments further comprising at least one excipient.

Embodiment 15. The composition according to embodiment 16, wherein said at least one excipient is selected from the group consisting of a bulking agent, a binder, a glazing agent, a sweetener and a flavour.

Embodiment 16. The composition according to embodiment 17, wherein said bulking agent is at least one bulking agent selected from the group consisting of xylitol, sorbitol, erythritol, maltitol, lactitol, inositol and mannitol, microcrystalline cellulose, glucose, isomalt, and starch, such as potato starch or corn starch.

Embodiment 17. The composition according to embodiment 17 or 18, wherein said binder is at least one binder selected from the group consisting of maltodextrin and sodium carboxymethylcellulose.

Embodiment 18. The composition according to any one of embodiments 17 to 19, wherein said glazing agent is at least one glazing agent selected from the group consisting of mono- and diglyceride of fatty acids, silicon dioxide, stearic acid, beeswax, candelilla wax, carnauba wax, shellac, microcrystalline wax, crystalline wax, lanolin, oxidized polyethylene wax, esters of colophonium, paraffin.

Embodiment 19. The composition according to any one of embodiments 17 to 20, wherein said sweetener is at least one sweetener selected from the group consisting of stevia, a steviol glycoside such as stevioside and rebaudioside, aspartame, sucralose, neotame, acesulfame potassium (Ace-K), saccharin, and advantame.

Embodiment 20. The composition according to any one of embodiments 17 to 21, wherein said flavour is at least one flavour selected from the group consisting of citric acid, lemon flavour, honeydew melon flavour, blueberry flavour, peach flavour, strawberry flavour, raspberry flavour, cola flavour, chocolate flavour, peppermint flavour, cherry flavour, lime flavour, orange flavour, vanilla flavour, tangerine flavour, liquorice flavour, apricot flavour, eucalyptus flavour, green tea flavour, ginger flavour and bilberry flavour.

Embodiment 21. The composition according to any one of the preceding embodiments, comprising:
(i) bulking agents in the form of xylitol and microcrystalline cellulose, isomalt,
(ii) binders in the form of maltodextrin and sodium carboxymethylcellulose,
(iii) glazing agents in the form of mono- and diglyceride of fatty acids and silicon dioxide,
(iv) a sweetener in the form of steviol glycoside, and
(v) optional flavours in the form of citric acid and lemon flavour.

Embodiment 22. The composition according to any one of the preceding embodiments, wherein said composition is in the form of a tablet, a capsule, powder, effervescents tablet, effervescents powder, a granulate, a microencapsulated product, a suspension, spray, a gel or a cream.

Embodiment 23. The composition according to any one of the preceding embodiments for use as a medicament.

Embodiment 24. The composition according to any one of the preceding embodiments for use in the treatment, prevention or alleviation of candidiasis.

Embodiment 25. The composition for use according to embodiment 24, wherein said candidiasisis is oral or vaginal candidiasis.

Embodiment 26. The composition for use according to embodiment 24, wherein said candidiasis is oral candidiasis.

Embodiment 27. The composition for use according to any one of embodiments 24 to 26, wherein said *Candida* spp. is selected from the list consisting of *Candida glabrata, Candida krusei, Candida tropicalis, Candida dubliniensis, Candida parapsilosis*, and *Candida albicans*.

Embodiment 28. The composition for use according to any one of embodiments 23 to 27 with the proviso that said candidiasis is not caused by *Candida albicans*.

Embodiment 29. The composition for use according to any of embodiments 23 to 28, wherein said composition comprises from $10^7$ to $10^{10}$ CFU lactobacilli per daily dose, such as $10^8$ to $10^9$ CFU lactobacilli per daily dose.

Embodiment 30. The composition for use according to embodiment 29, wherein said composition comprises at least $5 \times 10^7$ CFU *Lactobacillus rhamnosus* strain ERB 36 (DSM 32992) per daily dose.

Embodiment 31. The composition for use according to any of embodiments 23 to 30, wherein the composition is for administration at least once daily.

Embodiment 32. The composition for use according to any of embodiments 23 to 31, wherein the composition is for administration twice daily.

Embodiment 33. The composition for use according to any of embodiments 23 to 32, wherein the composition is for oral or vaginal administration.

Embodiment 34. A nutraceutical comprising the composition according to any one of the preceding embodiments.

Embodiment 35. A nutritional supplement comprising the composition according to any one of the preceding embodiments.

Embodiment 36. A container containing the composition according to any one of the preceding embodiments.

Embodiment 37. The container according to embodiment 36, wherein said container is selected from the list consisting of a blister pack, stick, bag, pouch, sachet and capsule.

Embodiment 38. The container according to embodiment 36 or 37 comprising one dose of said composition.

Embodiment 39. A kit comprising a plurality of containers according to any one of embodiments 36 to 38.

Embodiment 40. A method for reducing a *Candida* spp. infection in a subject, said method comprising the step of providing a therapeutic effective amount of a composition according to any of the proceeding embodiments to a subject in the need thereof.

Embodiment 41. The method according to embodiment 40, wherein said *Candida* spp. is selected from the list consisting of *Candida glabrata, Candida krusei, Candida tropicalis, Candida dubliniensis, Candida parapsilosis*, and *Candida albicans*.

Embodiment 42. The method according to embodiment 40 with the proviso that said *Candida* spp. is not *Candida albicans*.

Embodiment 43. A method for reducing, alleviating or preventing candidiasis in a subject, said method comprising the step of providing a therapeutic effective amount of a composition according to any of the proceeding embodiments to a subject in the need thereof.

Embodiment 44. The method according to embodiment 43, wherein said candidiasis is oral candidiasis or vaginal candidiasis.

Embodiment 45. The method according to embodiment 43 or 44, wherein said *Candida* spp. is selected from the list consisting of *Candida glabrata, Candida krusei, Candida tropicalis, Candida dubliniensis, Candida parapsilosis*, and *Candida albicans*.

Embodiment 46. The method according to any one of embodiments 43 to 45 with the proviso that said *Candida* spp. is not *Candida albicans*.

Embodiment 47. A method for maintenance of oral health in a subject, said method comprising the step of providing a therapeutic effective amount of a composition according to any of the proceeding embodiments to a subject in the need thereof.

Embodiment 48. The method according to embodiment 47, wherein said *Candida* spp. is selected from the list consisting of *Candida glabrata, Candida krusei, Candida tropicalis, Candida dubliniensis, Candida parapsilosis*, and *Candida albicans*.

Embodiment 49. The method according to embodiment 47 or 48 with the proviso that said *Candida* spp. is not *Candida albicans*.

Embodiment 50. The method according to any one of embodiments 40 to 49, wherein said composition comprises at least $10^7$ CFU lactobacilli per daily dose, such as in the range of $10^7$ to $10^{10}$ CFU lactobacilli per daily dose, such as $10^8$ to $10^9$ CFU lactobacilli per daily dose.

Embodiment 51. The method according to any one of embodiments 40 to 50, wherein said composition comprises *Lactobacillus rhamnosus* strain ERB 36 (DSM 32992).

Embodiment 52. The method according to any one of embodiments 40 to 51, wherein said composition further comprises *Lactobacillus rhamnosus* strain PB01 (DSM 14870) and/or *Lactobacillus curvatus* (EB10 DSM 32307).

Embodiment 53. The method according to any one of embodiments 40 to 52, wherein said composition comprises at least $5 \times 10^7$ CFU *Lactobacillus rhamnosus* strain ERB 36 (DSM 32992) per daily dose.

When describing the embodiments of the present invention, the combinations and permutations of all possible embodiments have not been explicitly described. Nevertheless, the mere fact that certain measures are recited in mutually different dependent claims or described in different embodiments does not indicate that a combination of these measures cannot be used to advantage. The present invention envisages all possible combinations and permutations of the described embodiments.

The terms "comprising", "comprise" and "comprises" herein are intended by the inventors to be optionally substitutable with the terms "consisting of", "consist of" and "consists of", respectively, in every instance.

EXAMPLES

Example 1

For *C. albicans*, probiotic interference has been demonstrated with probiotic lactobacilli, e.g. *L. rhamnosus* GR-1, and *L. reuteri* RC-14, ATCC PTA 5289, and DSM 17938, respectively. To our knowledge, only a few studies have looked into the antifungal effect of probiotic lactobacilli on non-*albicans Candida* species commonly found in the oral cavity (Jørgensen et al, 2017; Coman et al, 2014; Verdenelli et al., 2014 and Chew et al., 2015). The aim of this study was therefore to investigate the in vitro abilities of 14 lactobacilli strains to inhibit the growth of six opportunistic pathogenic oral *Candida* spp.

Materials and Methods

Strains and Culture Conditions 14 lactobacilli strains (Bifodan A/S, Hundested, Denmark) and six *Candida* spp. (clinical strains from the Department of Clinical Microbiology, Rigshospitalet, Copenhagen, Denmark, and control strains from the Culture Collection, University of Goteborg, Sweden) were used in this study (Table 1).

Prior to the in vitro study, the clinically isolated *Candida* strains were characterized by Matrix-assisted laser desorption/ionization time-of-flight (MALDI-TOF) mass spectrometry to confirm their identity (Table 1). The lactobacilli were initially cultured on de Man Rogosa Sharpe (MRS) agar (Oxoid Ltd., Basingstoke, Hampshire, UK) for 24 hours (h) in an anaerobic chamber at 37° C. (10% H2, 5% CO2 and 85% N2).

The *Candida* strains were cultured on BD Difco™ Sabouraud Dextrose (SD) agar (Becton, Dickinson and Company, Sparks, MD, USA) for 24 h in ambient air at 37° C. Agar Overlay Interference Test The growth inhibition assay was performed as described earlier (Jørgensen et al, 2017). In brief, one distinct colony of overnight cultured lactobacilli was transferred to 5 ml de Man Rogosa Sharp (MRS) broth (Oxoid Ltd., Basingstoke, Hampshire, UK) and incubated at 37° C. for 24 h under anaerobic conditions. The following day the lactobacilli were harvested by centrifugation at 2,000 rpm for 10 min. at room temperature. The supernatants of the lactobacilli strains were obtained after centrifugation and destroyed. The pellets were washed three times in phosphate-buffered saline (PBS) and resuspended in MRS broth. The OD was adjusted spectrophotometrically (Genesys™ 10S UV-Vis Spectrophotometer, Thermo Fisher Scientific, Waltham, MA, USA) to 1.8 at 630 nm (corresponding to approximately $10^9$ cfu/ml). The cultures were then serially diluted in MRS broth in 6-fold steps. One ml of the supernatants, undiluted suspensions and cell suspensions corresponding to approximately $10^7$ and $10^5$ CFU/ml were added to 24 ml sterilized molten MRS agar (~45° C.) in Petri dishes and the agar was allowed to solidify. The plates were incubated overnight at 37° C. under anaerobic conditions.

One single colony of each of the overnight cultured *Candida* strains was added to 5 ml broth and aerobically incubated at 37° C. for 24 h. The following day, one additional layer of 25 ml of molten sterile SD agar was poured on top of the MRS agar with grown lactobacilli, and was allowed to solidify and air-dry for 3 h in room temperature. The overnight cultured *Candida* strains were diluted in SD broth to a final OD of 0.2 at 500 nm. The *Candida* suspensions were stamped on the plates with a Steers steel-pin replicator (CMI-Promex ICN, Pedricktown, NJ, USA) and left to dry for 2 h at room temperature. The plates were subsequently aerobically incubated overnight at 37° C. As controls, the *Candida* strains were also stamped on top of plates with no lactobacilli within the bottom MRS agar layer.

Scoring

The assays were carried out in duplicates and repeated three times on different occasions. The results were evaluated in accordance with a modified version of Simark-Mattson et al. (2007) as:

0=complete inhibition (no visible colonies)

1=almost total inhibition (colonies slightly visible)

2=slight inhibition (colonies are clearly visible but smaller than at the control plate)

3=no growth inhibition (colonies equal to those at the control plate)

Two observers scored the plates independently, and in case of disagreement consensus was reached through discussion.

Statistical Analyses

All data were processed with SAS Enterprise guide software (version 7.1, SAS Institute Inc., Cary, NC, USA). A p-value <0.05 was considered statistically significant. For descriptive statistics, the growth inhibition scores for the lactobacilli at different doses are presented as the median score. The frequency of growth inhibition score 0-3 for each lactobacilli strain, dose, and *Candida* spp. is presented in percentage distribution.

Poisson regression tests were performed for the lactobacilli strains, *Candida* spp., and dose to predict the growth inhibition scores for these variables.

Based on the results from these tests, the four lactobacilli displaying the lowest growth inhibition scores were subjected to Chi-squared analyses.

Results

All the 14 lactobacilli had the ability to inhibit the growth of the *Candida* spp., however, there was a statistically significant difference in the ability based on score between the different lactobacilli strains (p<0.05) (Table 2 and 3).

A Poisson regression test was run to predict the growth inhibition score for each lactobacilli strain based on the growth inhibition experiments. The test showed that *L. rhamnosus* DSM 32992 displayed the best growth inhibition properties against the *Candida* spp. displaying the highest amount of score 0 and 1, followed by *L. rhamnosus* DSM 32991, *L. jensenii* 22B42, and *L. rhamnosus* PB01, respectively (Table 3 and 4). The four strains all had very good ability to inhibit the growth of the *Candida* spp. based on score. However, there was a statistically significant difference between the four strains (p<0.0001, chi-squared). *L. rhamnosus* DSM 32992 was statistically significantly better at inhibiting the *Candida* spp. compared with the other three lactobacilli strains (p<0.001). There was no statistically significant difference between *L. rhamnosus* DSM 32991 and *L. jensenii* 22B42 (p=0.109) and borderline statistically significant difference between *L. rhamnosus* DSM 32991 and *L. rhamnosus* PB01 (p=0.059). Likewise, there was borderline statistically significant difference between *L. jensenii* 22B42 and *L. rhamnosus* PB01 (p=0.067) (Table 4).

Similarly, Poisson regression test was performed to predict the best dose in order to inhibit the growth. The results revealed an almost equal effect for dose $10^9$ and $10^7$ CFU/ml, the latter being slightly superior (NS). Dose $10^5$ CFU/ml appeared to be the weakest dose for growth inhibition (Table 2 and 5).

Poisson regression for the *Candida* spp. showed that *C. parapsilosis* CCUG 56136 and *C. parapsilosis* clinical strain was inhibited to the highest extend. *C. krusei* CCUG 47037 and *C. krusei* clinical strain were the hardest strains to inhibit, since most colonies were only slightly inhibited or not inhibited (score 2 and 3), (Table 2 and 6).

Conclusion

In conclusion, all the lactobacilli tested in this in vitro study showed the ability to inhibit the growth selected *Candida* spp. However, the lactobacilli strains with the best growth inhibition capabilities were *L. rhamnosus* DSM 32992, *L. rhamnosus* DSM 32991, *L. jensenii* 22B42, and *L. rhamnosus* PB01, respectively. The optimal dose for the lactobacilli in order to provide growth inhibition was $10^7$ CFU/ml. The mostly inhibited *Candida* spp. were *C. parapsilosis* CCUG 56136 and *C. parapsilosis* clinical strain, whereas *C. krusei* CCUG 56126 and *C. krusei* clinical strain were the hardest strains to growth inhibit.

TABLE 1

| List of microbes used in the study | |
|---|---|
| Genera | Species |
| *Lactobacillus* | *Lactobacillus crispatus* 23B33 |
| | *Lactobacillus crispatus* NEU 458 DSM 15224 |
| | *Lactobacillus fermentum* S1P2 |
| | *Lactobacillus fermentum* S1P1 |
| | *Lactobacillus jensenii* 12B1 |
| | *Lactobacillus jensenii* 22B42 |
| | *Lactobacillus rhamnosus* PB01 DSM 14870 |
| | *Lactobacillus rhamnosus* NEU 427 |
| | *Lactobacillus rhamnosus* ERB18, P2-1, DSM 32991 |
| | *Lactobacillus rhamnosus* ERB 36, P5-1 DSM 32992 |
| | *Lactobacillus gasseri* EB01 DSM 14869 |
| | *Lactobacillus curvatus* EB10 DSM 32307 |
| | *Lactobacillus acidophilus* EB03 DSM 15527 |
| | *Lactobacillus paracasei* S1-P3 |
| *Candida* | Control CCUG strains *Candida albicans* CCUG 46390 |
| | *Candida dubliniensis* CCUG 48722 |
| | *Candida glabrata* CCUG 63819 |
| | *Candida krusei* CCUG 56126 |
| | *Candida parapsilosis* CCUG 56136 |
| | *Candida tropicalis* CCUG 47037 |
| | Clinical isolates *Candida albicans* CBS 562 NT |
| | *Candida dubliniensis* 41_3 ZZMK |

TABLE 1-continued

List of microbes used in the study

| Genera | Species |
| --- | --- |
| | Candida glabrata CBS 863 |
| | Candida krusei RV 491 |
| | Candida parapsilosis 26 PBS |
| | Candida tropicalis DSM 7524 |

Example 2

Material and Methods

Figure 2:
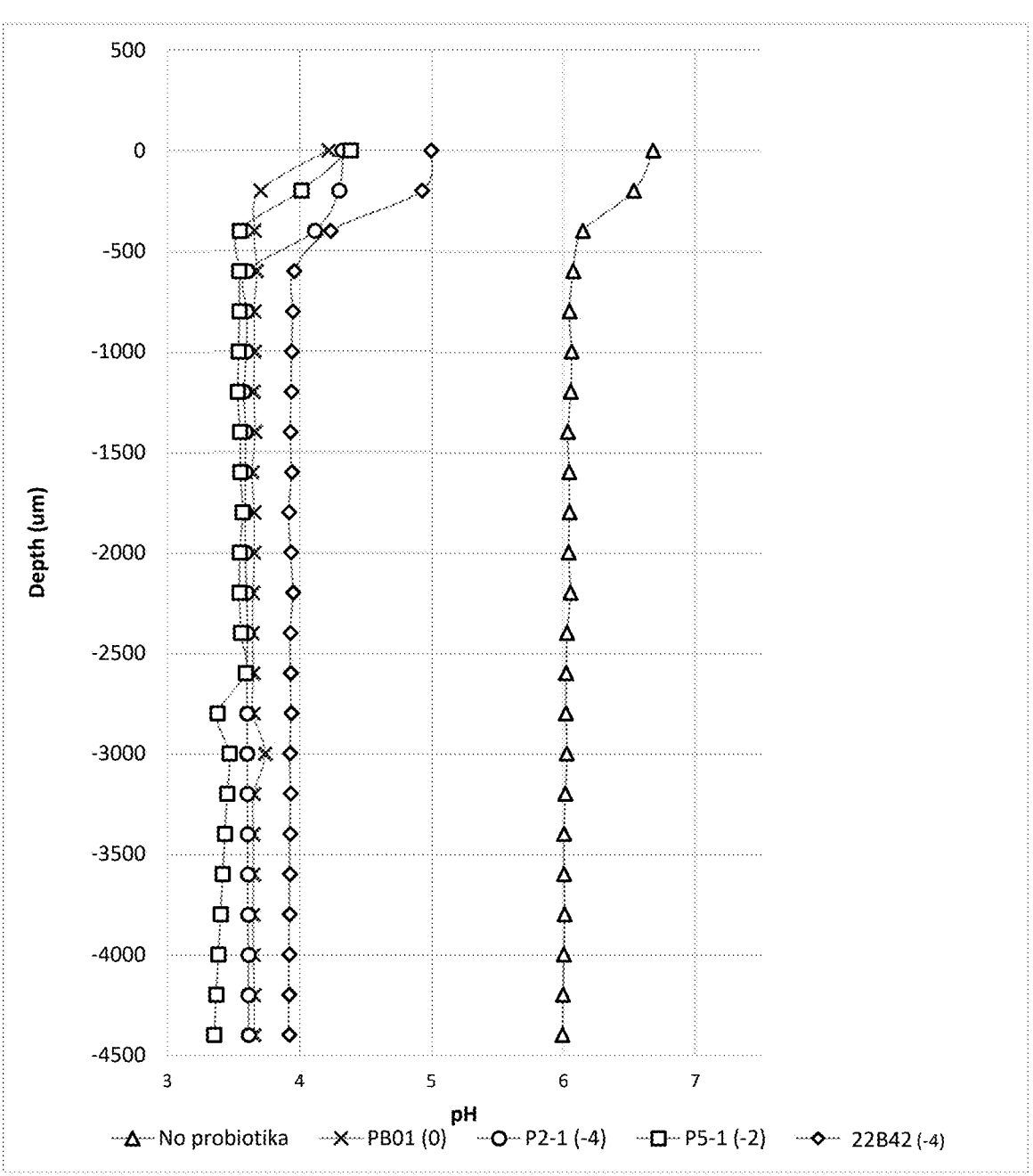
FIG. 2 pH measurements in agar plate with *C. dubliniensis*.
Figure 3:
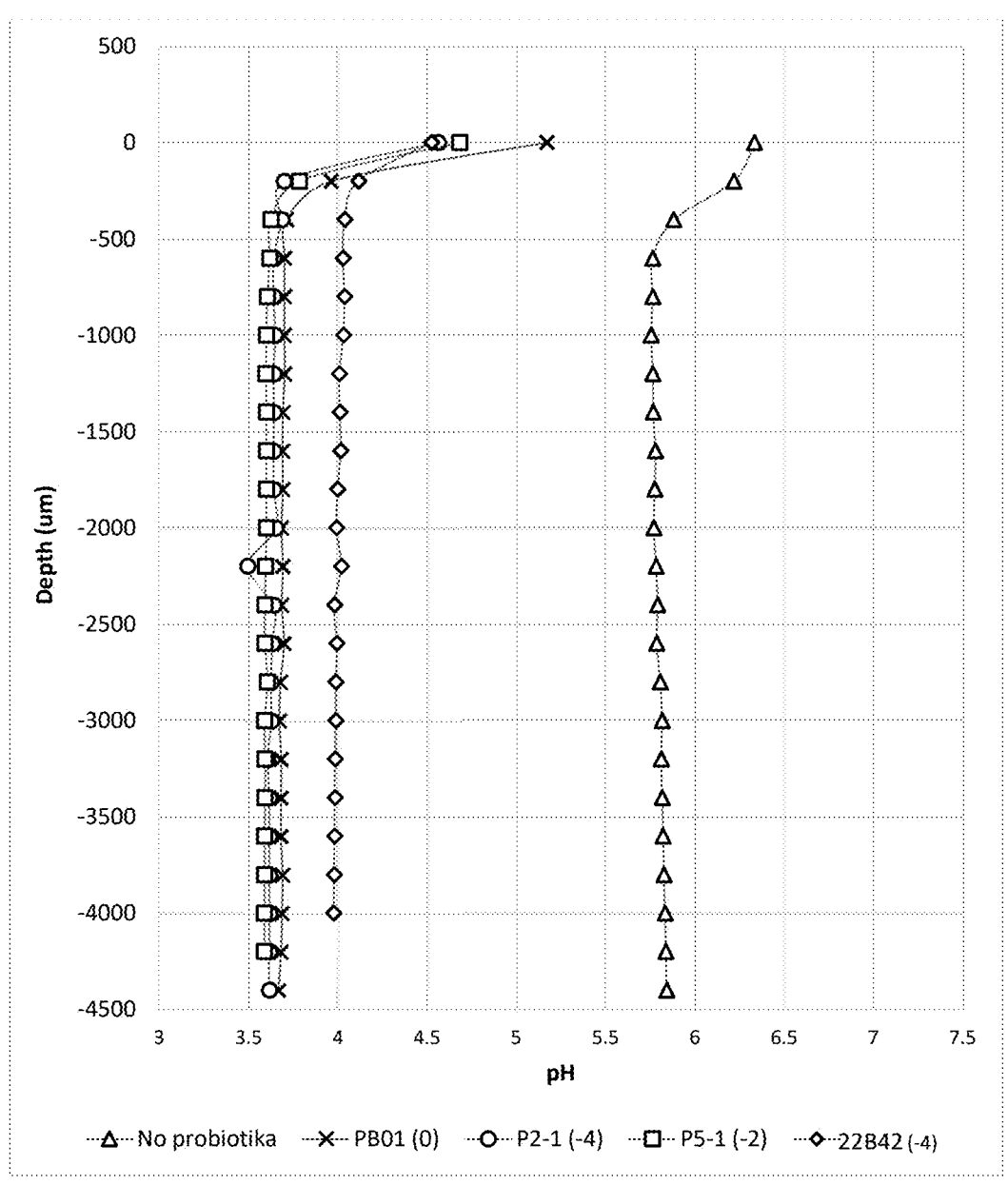
FIG. 3 pH measurements in agar plate with *C. albicans*.
Figure 4:
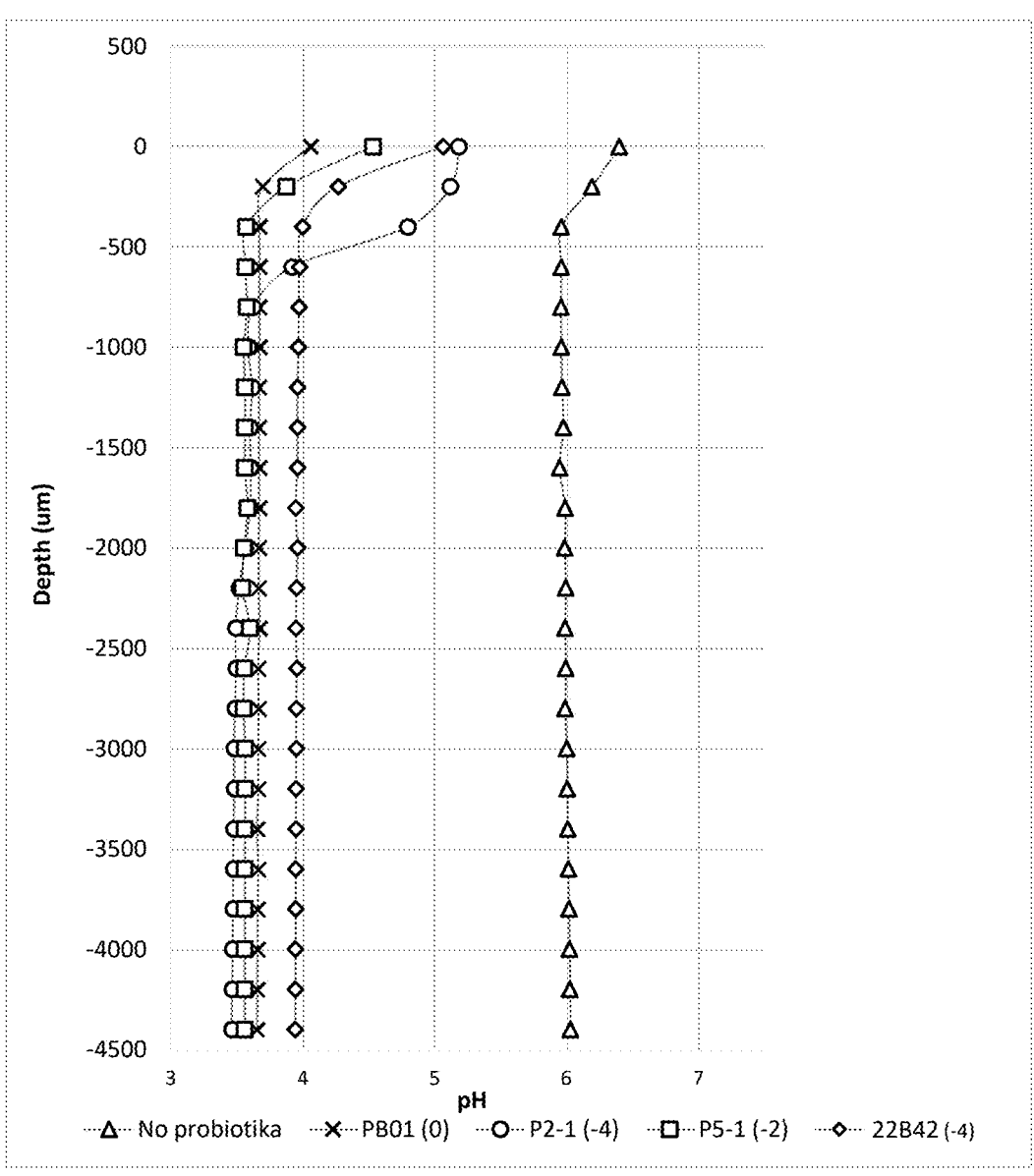
FIG. 4 pH measurements in agar plate with *C. glabrata*.
Figure 5:
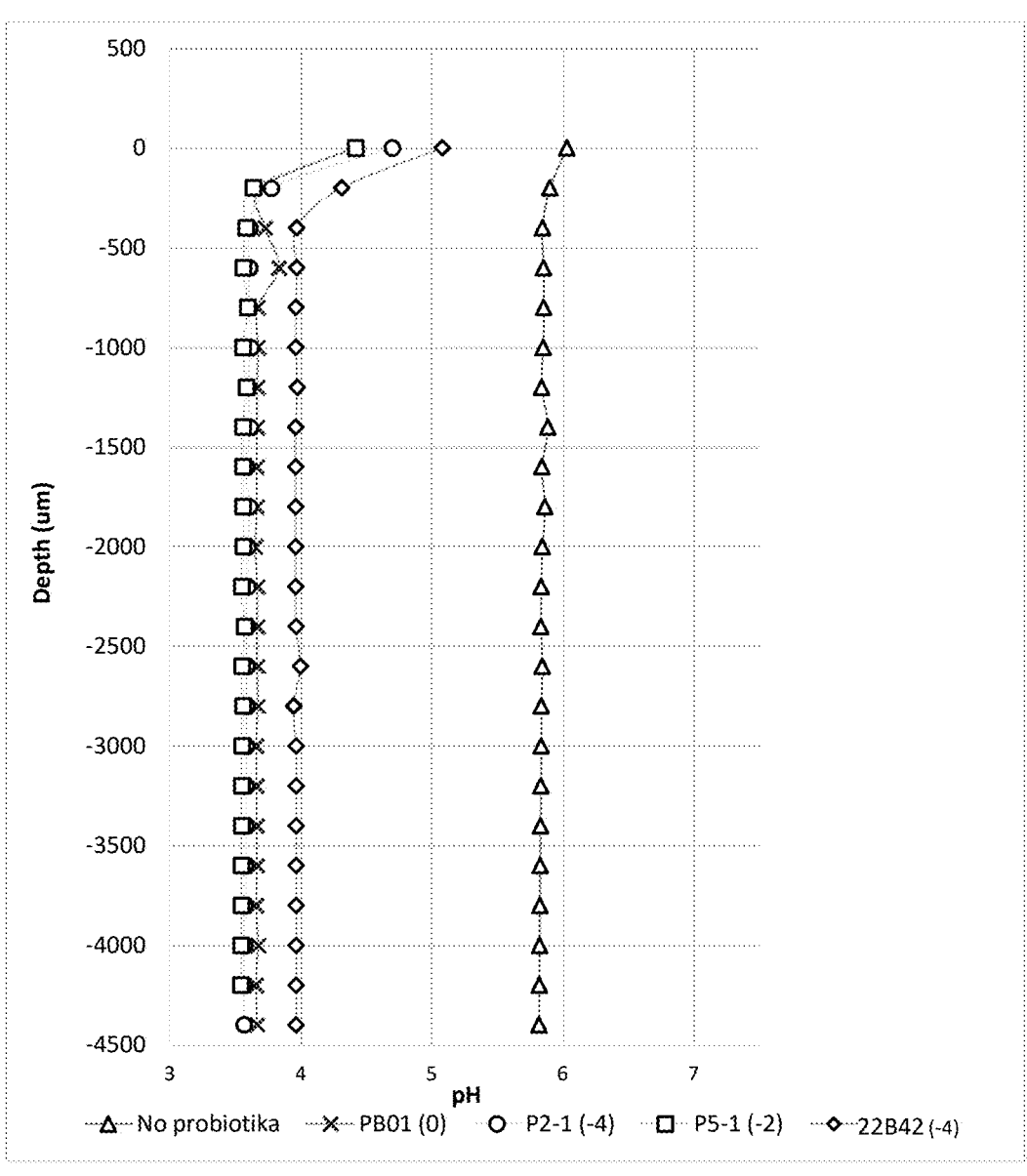
FIG. 5 pH measurements in agar plate with *C. parapsilosis*.
Figure 6:
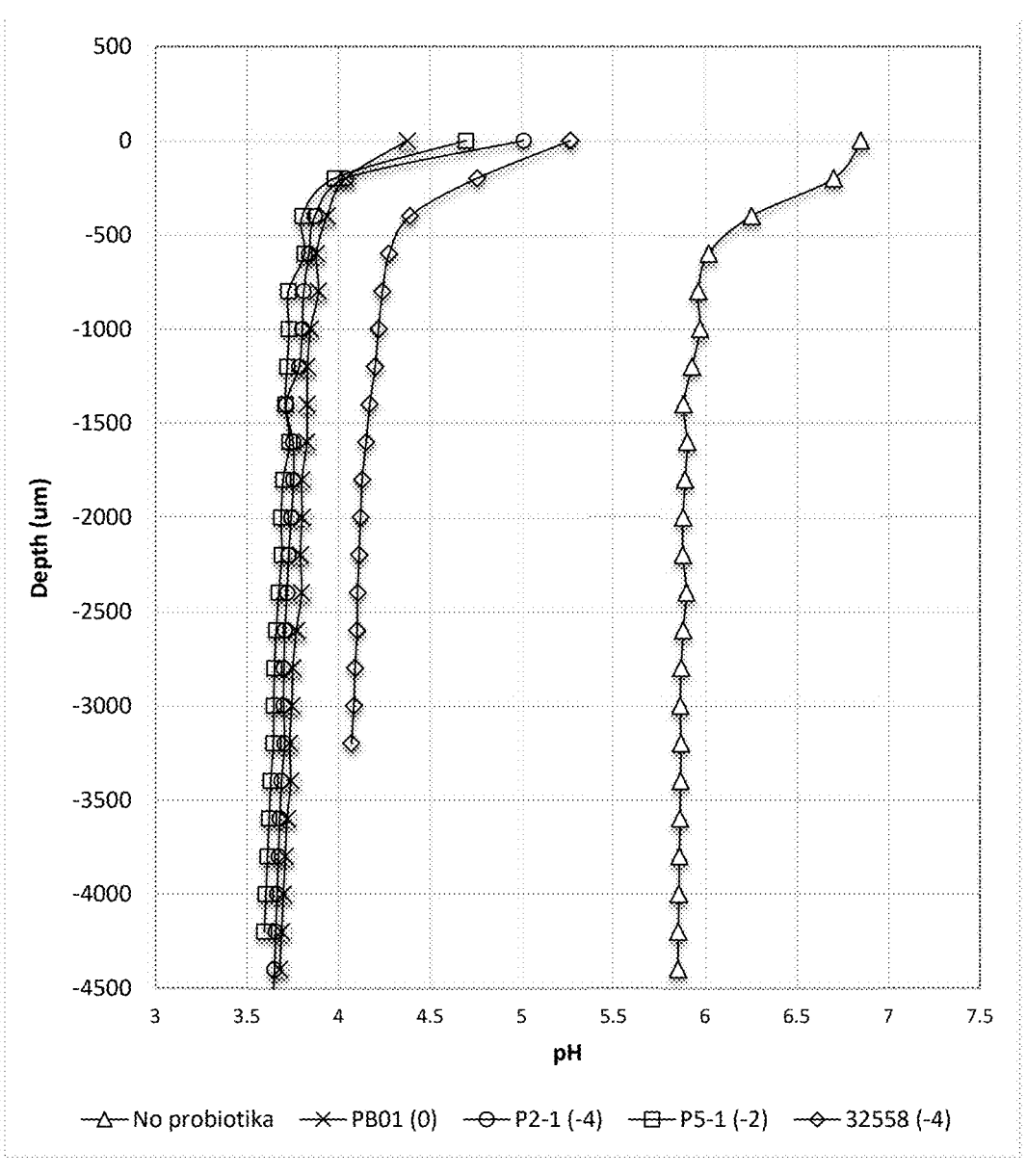
FIG. 6 pH measurements in agar plate with *C. tropicalis*.
Figure 7:
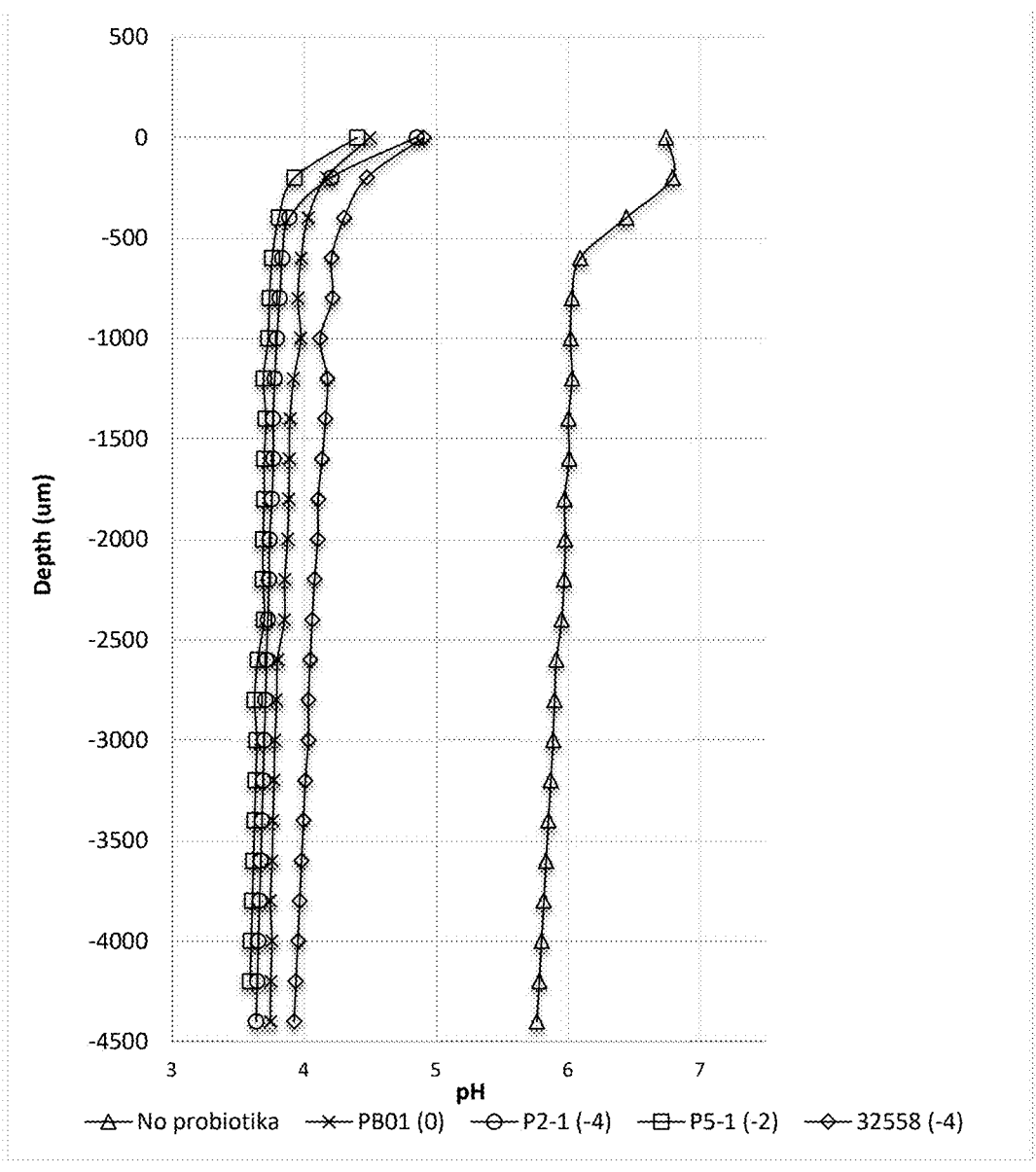
FIG. 7 pH measurements in agar plate with *C. krusei*.

Acid production (measured by pH) of the four best performing lactobacilli and the effect of pH on *Candida* growth was measured with a pH microelectrode and a reference electrode (pH-100 and ref-100; Unisense A/S, Århus, Denmark) using a modification of a previously described procedure (Jørgensen et al., 2017) in selected plates from the growth inhibition test. The electrodes were mounted in a motorized PC-controlled profiling setup (MM33 and MC-232, Unisense A/S), and positioning and data acquisition were controlled by dedicated software (Sensortrace Pro 2.0, Unisense A/S). The pH and reference electrodes were calibrated with buffers of pH 4 and 7 at room temperature. The pH microelectrode had a detection limit of 0.1 pH units. The pH was measured on the final day of the growth inhibition test. Selection of the plates was based on the results from the interference test; the plates with the highest inhibition scores for each lactobacilli strain was selected regardless of concentration. pH was measured through dense, slightly-inhibited colonies of *Candida* (*C. krusei* and *C. tropicalis*) and through vague, almost completely inhibited colonies (*C. albicans, C. glabrata, C. dubliniensis*, and *C. parapsilosis*) incubated on plates with *L. rhamnosus* DSM 32992 (P5-1), *L. rhamnosus* DSM 32991 (P2-1), *L. jensenii* 22B42, and *L. rhamnosus* PB01, respectively. In addition, pH was measured in control plates containing only the lactobacilli in the bottom agar layer, but with no *Candida* incubated, in a control plate with *Candida* strains but without lactobacilli, and lastly at a control agar plate without lactobacilli or *Candida* strains. Before measuring, the pH and reference electrodes were placed approximately 2 mm above the surface of the *Candida* colonies. The electrodes were set to move in steps of 100 µm, and pH was measured from the surface of the colonies and then for every 100 µm until the depth of 4.5 mm into the agar to make sure the sensors had reached the bottom agar layer containing the lactobacilli.
Results Results of the pH microsensor measurements are shown in FIGS. 1-7. Similar pH profiles appeared for all four lactobacilli strains incubated with the *Candida* spp.; however, measurements from *L. rhamnosus* DSM 32992 (P5-1) and *L. rhamnosus* DSM 32991 (P2-1) generally showed the lowest pH values in all plates. pH of the agar alone and in control plates with the four lactobacilli strains without *Candida* spp. is presented in FIG. 1. pH of the agar alone was 5.8, and pH in the agar plates with the lactobacilli ranged from 3.5-3.8. pH measured through the dense colonies of *C. krusei* and *C. tropicalis* (FIGS. 6 and 7) was approximately 6.8 at the surface of the colonies in the plate without lactobacilli, reaching 5.8 around 700-1000 µm down in the agar. For the measurements with the lactobacilli, pH at the surface of the *Candida* colonies ranged between 4.4-4.9 for *C. krusei*, and 4.4-5.3 for *C. tropicalis*, and slowly becoming more acidic throughout the agar layers approaching approximately pH 3.5 in the bottom agar layer. For the rest of the *Candida* spp., where colonies were almost completely inhibited (FIGS. 2-5), pH reached an acidity level comparable with the control plate displaying vertical pH curves only a few 100 µm under the surface and remained stable throughout the agar layers.
Conclusions

*L. rhamnosus* DSM 32992 (P5-1) and *L. rhamnosus* DSM 32991 (P2-1) showed the lowest pH values indicating the highest acid production of the selected lactobacilli. This corresponds to the results from the inhibition test, where these two *Lactobacillus* strains exhibited the best inhibition abilities of the tested lactobacilli against the *Candida* spp. confirming that acid production plays an important role in inhibiting *Candida* growth. *C. krusei* and *C. tropicalis* showed a tendency towards neutralizing the acids in the upper part of the agar indicating an ability to inhibit the acidification caused by the lactobacilli to ensure their survival.

REFERENCES

Zheng et al., Int. J. Syst. Evol. Microbiol. 2020, 70:2782-2858.
Jørgensen et al., Journal of Oral Microbiology, 2017, 9(1): 1274582.
Coman et al., J. Appl. Microbiol., 2014, 117(2): 518-27.
Verdenelli et al., J. Appl. Microbiol., 2014, 116(5): 1297-307.
Chew et al., J. Appl. Microbiol., 2015, 118(5): 1180-90.
Simark-Mattsson et al., Eur. J. Oral. Sci.; 2007, 115(4): 308-14.

The invention claimed is:

1. A *Lactobacillus rhamnosus* strain ERB 36 having accession number DSM 32992, wherein said strain is in a lyophilized, spray dried, vacuum dried or microencapsulated form or any combination thereof.

2. A culture broth comprising *Lactobacillus rhamnosus* strain ERB 36 having accession number DSM 32992, wherein said broth is in a lyophilized, spray dried, vacuum dried or microencapsulated form or any combination thereof.

3. The culture broth according to claim 2, further comprising at least one lactobacilli sp. selected from the group consisting of *Lactobacillus rhamnosus* strain ERB18 having accession number DSM 32991, *Lactobacillus rhamnosus* strain PB01 having accession number DSM 14870 and *Lactobacillus curvatus* EB10 having accession number DSM 32307.

4. A composition comprising *Lactobacillus rhamnosus* strain ERB 36 having accession number DSM 32992, wherein said strain is in a lyophilized, spray dried, vacuum dried or microencapsulated form or any combination thereof, wherein said composition is in the form of a tablet, a capsule, an effervescent tablet, an effervescent powder, a microencapsulated product, a gel or a cream.

5. The composition according to claim 4, comprising at least one further lactobacilli sp. selected from the group consisting of *Lactobacillus rhamnosus* strain ERB18 having accession number DSM 32991, *Lactobacillus rhamnosus* strain PB01 having accession number DSM 14870 and *Lactobacillus curvatus* EB10 having accession number DSM 32307.

6. The composition according to claim 4, wherein said composition comprises from $10^5$ to $10^{13}$ CFU of lactobacilli per gram of said composition.

7. The composition according to claim 4, further comprising a bulking agent, a binder, a glazing agent, a sweetener or a flavour.

8. A method comprising administering to a subject in need of a probiotic:

a) *Lactobacillus rhamnosus* strain ERB 36 having accession number DSM 32992, wherein said strain is in a lyophilized, spray dried, vacuum dried or microencapsulated form or any combination thereof; or, b) the composition of claim 4.

9. A method of treating or alleviating candidiasis in a subject, comprising administering *Lactobacillus rhamnosus* strain ERB 36 having accession number DSM 32992, wherein said strain is in a lyophilized, spray dried, vacuum dried or microencapsulated form or any combination thereof to a subject in need thereof.

10. The method according to claim 9, wherein said candidiasis is oral or vaginal candidiasis.

11. The method of claim 9, wherein said candidiasis is caused by a *Candida* spp. selected from the group consisting of *Candida glabrata, Candida krusei, Candida tropicalis, Candida dubliniensis, Candida parapsilosis*, and *Candida albicans*.

12. A container containing *Lactobacillus rhamnosus* strain ERB 36 having accession number DSM 32992, wherein said strain is in a lyophilized, spray dried, vacuum dried or microencapsulated form or any combination thereof, or the composition according to claim 4.

13. The container according to claim 12, wherein said container is a blister pack, stick, bag, pouch, sachet, or capsule.

14. A method of treating or alleviating candidiasis in a subject, comprising administering the composition of claim 4 to a subject in need thereof.

15. The composition according to claim 4, comprising at least one further lactobacilli sp. selected from the group consisting of *Lactobacillus rhamnosus* strain ERB18 having accession number DSM 32991, *Lactobacillus rhamnosus* strain PB01 having accession number DSM 14870 and *Lactobacillus curvatus* EB10 having accession number DSM 32307.

16. A method of treating or alleviating candidiasis in a subject, comprising administering the composition of claim 15 to a subject in need thereof.

\* \* \* \* \*